US012100565B2

(12) United States Patent
Zeller et al.

(10) Patent No.: US 12,100,565 B2
(45) Date of Patent: Sep. 24, 2024

(54) FOOT SWITCH FOR MEDICAL DEVICES

(71) Applicant: KARL STORZ SE & Co. KG, Tuttlingen (DE)

(72) Inventors: Marco Zeller, Tuttlingen (DE); Alexander Sabo, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 941 days.

(21) Appl. No.: 17/030,699

(22) Filed: Sep. 24, 2020

(65) Prior Publication Data

US 2021/0090828 A1 Mar. 25, 2021

(51) Int. Cl.
| H01H 21/26 | (2006.01) |
| A61B 90/00 | (2016.01) |
| G05F 1/625 | (2006.01) |
| H01H 13/16 | (2006.01) |
| H04B 1/02 | (2006.01) |
| H04B 1/06 | (2006.01) |

(52) U.S. Cl.
CPC ............. *H01H 21/26* (2013.01); *A61B 90/08* (2016.02); *G05F 1/625* (2013.01); *H01H 13/16* (2013.01); *H04B 1/02* (2013.01); *H04B 1/06* (2013.01)

(58) Field of Classification Search
CPC ... H04B 1/00; H04B 1/02; H04B 1/06; H01H 13/00; H01H 13/16; H01H 21/26; G05F 1/00; G05F 1/625; A61B 90/00; A61B 90/08
USPC ....................................................... 200/86.5
See application file for complete search history.

(56) References Cited

U.S. PATENT DOCUMENTS

2007/0078539 A1* 4/2007 Kuhner .................. H01H 3/14
700/90

FOREIGN PATENT DOCUMENTS

| DE | 203 12 016 U1 | 10/2003 |
| DE | 103 51 199 B3 | 6/2005 |
| EP | 0 864 293 A1 | 9/1998 |
| EP | 1 503 265 A1 | 2/2005 |
| WO | 2005/043569 A1 | 5/2005 |

OTHER PUBLICATIONS

Search Report for DE 10 2019 125 669.0, dated May 22, 2020 (7 pp.).
Extended Search Report for EP 20198226.1, Dated Nov. 10, 2020 (8 pp.). (In German).

* cited by examiner

*Primary Examiner* — Anthony R Jimenez
(74) *Attorney, Agent, or Firm* — Eversheds Sutherland (US) LLP

(57) ABSTRACT

The present application provides a foot actuation system for controlling one or more medical devices using a foot. The foot actuation system includes a communications unit and a number of actuation units. Each actuation unit includes a user interface for receiving an actuation information item generated by means of a foot, a mechanical connection apparatus for releasable mechanical connection to the communications unit, and a signal transmitter for transmitting a signal representing the actuation information item. The communications unit includes a mechanical connection apparatus for releasable mechanical connection to the actuation units, a signal receiver for receiving the signals representing the actuation information items, and a control signal transmitter for transmitting a control signal to a medical device.

9 Claims, 4 Drawing Sheets

Fig. 7
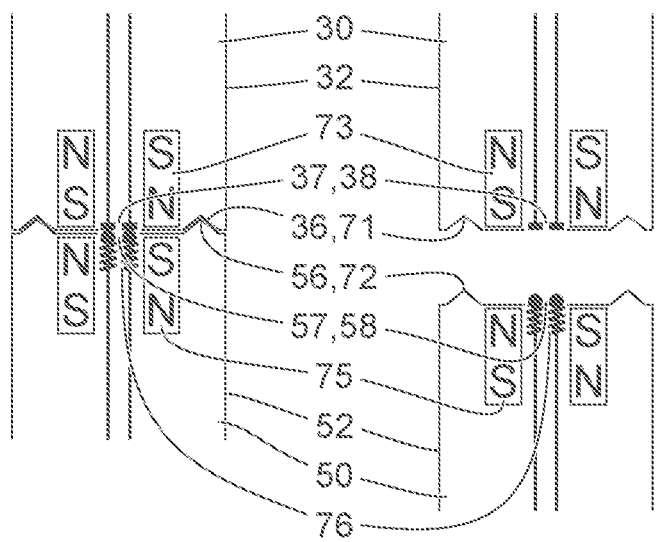
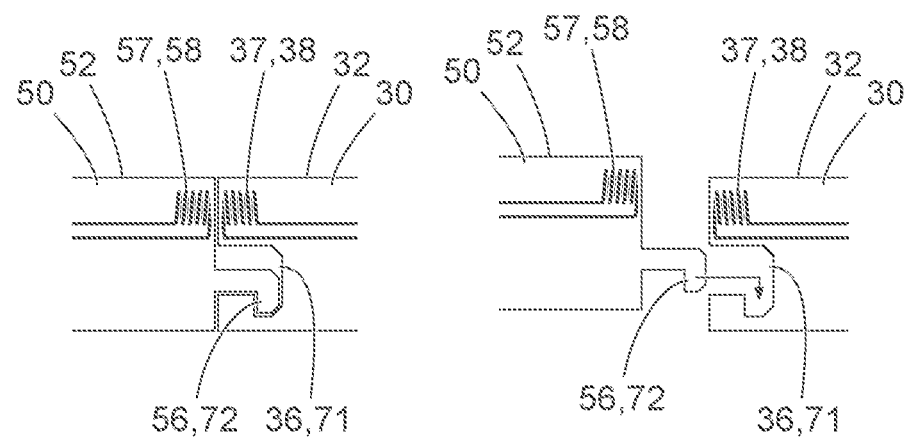
Fig. 8A　　　　　　　Fig. 8B

FOOT SWITCH FOR MEDICAL DEVICES

The present invention relates to a foot switch for controlling one or more medical devices.

Numerous medical devices have functions that can be triggered, activated and deactivated, modified, modulated or controlled in some other way by medical staff. To this end, user interfaces are provided on medical devices or the medical devices are able to be coupled with user interfaces. Foot switches are conventional in many applications in order to allow medical staff to control one or more functions even in the case where no hands are free for a manual action at a user interface.

U.S. Pat. No. 4,705,500 describes an ophthalmological apparatus for irrigation and aspiration, comprising a hand-held device ("hand held device") and a control unit 20 that is operable by means of a foot ("foot-operable control unit"), wherein the control unit 20 comprises a foot pedal 24 (column 1, line 55—column 2, line 24; column 3, lines 32-44; column 5, lines 43-57). The foot-operable control unit 20 further comprises a power source 100, in particular a battery (column 5, lines 43-57).

US 2012/0064483 A1 describes a foot switch system ("foot switch system") with a foot switch apparatus ("foot switch device") 10 for operating a medical treatment apparatus ("medical treatment apparatus") 12 (paragraphs [0002], [0013], [0025], etc.). The foot switch apparatus 10 can be connected to the medical treatment apparatus 12 in wireless fashion ("wireless") or by means of a cable ("hard wired") (paragraphs [0029], [0030]).

An object of the present invention consists of developing an improved foot switch system.

This object is achieved by the subject matter of the independent claims.

Developments are specified in the dependent claims.

A foot actuation system for controlling one or more medical devices using a foot comprises a communications unit and a plurality of actuation units, wherein each actuation unit comprises a user interface for capturing an actuation information item generated by means of a foot, a mechanical connection apparatus for releasable mechanical connection to the communications unit and a signal transmitter for transmitting a signal representing the actuation information item, and wherein the communications unit comprises a mechanical connection apparatus for releasable mechanical connection to a plurality of actuation units, a signal receiver for receiving the signals representing the actuation information items, and a control signal transmitter for transmitting a control signal to a medical device.

By way of example, the foot actuation system is provided and embodied for controlling a light source for an endoscope, an exoscope or a microscope, a camera control unit (CCU), an insufflator or any other pump for supplying or removing a fluid, an electric power source for electrosurgery or any other medical device.

The entire foot actuation system is provided for arrangement on the floor or near the floor of an operating theater, a treatment room in a medical practice or in any other medical establishment.

Both the communications unit and each individual one of the plurality of actuation units are respectively embodied as a unit, in particular, which is neither taken apart nor opened during the envisaged use, during cleaning and during the configuration of the foot actuation system. In particular, the communications unit and each actuation unit can only be opened and/or taken apart by means of a tool which is not included in the objects typically present in an operating theater or any other medical treatment room, for example by means of a screwdriver. Therefore, both the communications unit and each individual actuation unit are provided to be used and handled as an unchangeable unit by medical staff.

In particular, the communications unit and the actuation units are provided and embodied to be put together by medical staff as desired in order to form one of a plurality of different, possible configurations of the foot actuation system. These possible configurations of the foot actuation system can differ in terms of the number of actuation units mechanically connected to the communications unit and/or in the arrangement within the foot actuation system of the actuation units and optionally also of the communications unit.

The mechanical connection apparatuses of the communications unit and of the actuation units are provided and embodied for a non-destructive releasable mechanical connection. Therefore, releasing the mechanical connection between the mechanical connection apparatuses of a communications unit and an actuation unit or between two adjacent actuation units does not destroy or damage either of the two mechanical connection apparatuses and, in particular, produces no wear, or only little wear, either, and so the mechanical connections can be established and released again very frequently—as measured in terms of the processes in hospitals, medical practices and other medical establishments: virtually as often as desired.

In particular, the mechanical connection apparatuses of the communications unit and of the actuation units are embodied in such a way that any connection between the communications unit and one actuation unit or between two actuation units can be quickly and reliably established or released or separated within a few seconds by means of one or more hand movements. To this end, the mechanical connection apparatuses are embodied, for example, the latching connections, screw connections, quarter-turn connections (often referred to as bayonet connections), magnetic connections or hook connections, or comprise hook-and-loop fasteners or the like.

The communications unit and each actuation unit can be embodied in such a way that a plurality of actuation units can each be connected directly to the communications unit at the same time. Here, the actuation units respectively connected directly to the communications unit are arranged next to one another in particular, i.e., in a straight or curved line. As an alternative or in addition thereto, each actuation unit can be provided and embodied for being directly connected to one or more further actuation units and hence being indirectly connected to the communications unit.

The communications unit differs from the actuation units, in particular in that it comprises a control signal transmitter for transmitting a control signal to one or more medical devices or to a system of medical devices which, for example, are interconnected by a Storz Communication Bus SCB or any other bus or an Ethernet or any other communications medium. That is to say, there is no direct communication between an actuation unit and a medical device; instead, any communication between an actuation unit and a medical device takes place via the communications unit. The communications unit communicates with all actuation units mechanically connected thereto. In particular, this means that the communications unit receives from all actuation units mechanically connected to the communications unit signals representing the actuation information items. Communication in the reverse direction, i.e., from the communications unit to the actuation units, is optional.

The communications unit can further differ from the actuation units by virtue of, for example, comprising a plurality of mechanical connection apparatuses, which are all the same, for releasable direct mechanical connection to respectively one actuation unit.

Each actuation unit comprises one or more user interfaces that are easily actuatable by a foot, each in the form of a button or a pedal or any other movable outer surface region or a touch-sensitive or contact-pressure-capturing surface region. Each individual user interface can capture a movement, for example a button being pushed, a pedal being pivoted about a horizontal axis, a roller being rotated about a horizontal axis or a surface region of the actuation unit being rotated about a vertical axis, or simply a touch or an exerted force and can generate either a binary signal or an analog or digital proportional signal. A proportional signal can facilitate a distinction between a plurality of or many different actuation travels, pivot or rotation angles or force values.

Each actuation unit differs from the communication unit in that, in particular, an actuation unit comprises a signal transmitter for transmitting a signal representing the actuation information item to the communications unit. In contrast thereto, the communications unit comprises a control signal transmitter for transmitting a control signal to one or more medical devices. By way of example, the control signal combines the signals, which are provided by the actuation units, representing the actuation information items.

Optionally, the communications unit can also comprise one or more user interfaces for receiving actuation information items generated by means of a foot. Alternatively, the communications unit comprises no user interface.

The communications unit can capture the arrangement of the actuation units and hence the current configuration of the foot actuation system. The current configuration of the foot actuation system captured by the communications unit can be displayed on, for example, a screen at any time in order to make the "blind" actuation of the actuation units easier for medical staff.

The foot actuation system can facilitate a largely free configuration in terms of the adaptation to the medical device or devices to be controlled and/or to the preferences or needs of medical staff. Particularly when a system of medical devices is extended by one or more further medical devices, the foot actuation system can be supplemented by one or more actuation units in order to control additional functions of the extended system of medical devices. A repair can also be simplified because it is not necessary to replace the entire foot actuation system but only a single unit of the same.

As a result of the mechanical connections between the actuation units and the communications unit, the foot actuation system, in its respectively chosen configuration, is present as a contiguous and, in particular, inherently rigid object. An individual actuation unit cannot be inadvertently displaced in such a way that a subsequent "blind" retrieval with the foot is made more difficult. As a result of the greater mass of the foot actuation system in comparison with an individual actuation unit, an inadvertent displacement of the entire foot actuation system in its chosen configuration is less probable.

Using the communications unit to bundle the communication between the actuation units and the medical devices to be controlled can significantly reduce the number of communication paths, in particular the number of cables required.

In the case of a foot actuation system as described herein, the communications unit comprises, in particular, a plurality of mechanical communications apparatuses next to one another, for releasable mechanical connection to respectively one actuation unit.

In particular, the mechanical connection apparatuses are arranged in a straight or curved line and, for example, equidistantly from the respective closest adjacent mechanical connection apparatuses. The communications unit can comprise a plurality of lines of mechanical connection apparatuses, for example at longitudinal sides of the communications unit facing away from one another. By way of example the communications unit comprises two, three, four, five, six or more mechanical connection apparatuses next to one another in order to be connected to a corresponding number of actuation units, or else a fewer number of actuation units where necessary, in each case in direct mechanical fashion.

In the case of a foot actuation system as described herein, the mechanical connection apparatus and the signal transmitter are integrated or arranged rigidly relative to one another, in particular at each of the plurality of actuation units, wherein respectively one mechanical connection apparatus and one signal receiver are integrated or arranged rigidly relative to one another at the communications unit.

At each of the plurality of actuation units, the mechanical connection apparatus and the signal transmitter, in particular, are integrated in a mechanical and electrical plug-in and/or screw connector or in a mechanical and electrical plug-in and quarter-turn connector. At the communications unit, the mechanical connection apparatus and the signal receiver, in particular, are integrated in a mechanical and electrical plug-in and/or screw connector or in a mechanical and electrical plug-in and quarter-turn connector. Alternatively, the signal transmitters and the signal receivers can be respectively arranged next to, above or below the associated mechanical connection apparatus, but in a rigid, i.e., immovable, fashion relative thereto.

In the case of a foot actuation system as described herein, the communications unit comprises, in particular, a plurality of power transmitters for transmitting power to one actuation unit in each case, wherein each of the plurality of actuation units comprises a power receiver for receiving power from the communications unit.

The power transmitters and the power receivers are provided and embodied, in particular, for transmitting and receiving electric power, respectively. The signal receivers can be partly or completely identical to the respective power transmitters of the communications unit. By way of example, this is the case if each actuation unit merely comprises a switch, which can be open or closed, or a potentiometer, which has a variable resistance, or capacitor, which has a variable capacitance, or a coil, which has a variable inductance. Using only two electric lines, electric power can be transmitted by the communications unit to the actuation unit and the state of the switch or the resistance of the potentiometer or the capacitance of the capacitor or the inductance of the coil can be captured. Thus, in this case, one pair of electrical contacts on the communications unit can form a power transmitter and, at the same time, a signal receiver and one pair of electrical contacts at an actuation unit can form a power receiver and simultaneously a signal transmitter, respectively.

Alternatively, the power and the signal can be transmitted by way of three or more lines. Even in the case of an inductive or capacitive transmission, it is possible to transmit both power from the communications unit to the actuation unit and a signal representing the actuation information item from the actuation unit to the communications units by way of a respective coil on part of the communications unit and on part of the actuation unit or by a respective pair of planar electrodes on part of the communications unit and on part of the actuation unit. Alternatively, the power transmission device can differ from the signal receiver device on part of the communications unit and the power receiver can differ from the signal transmitter on part of the actuation unit.

As an alternative, both the power and the signals representing the actuation information can alternatively be transmitted optical or acoustic fashion. In the case of an optical transmission of power and signal, provision can be made of a single transmission path for both or provision can be made of different transmission paths. In the case of an acoustic transmission of power and signal, provision can be made of a single transmission path for both or provision can be made of different transmission paths.

In the case of a foot actuation system as described herein, the mechanical connection apparatus and the power receiver are integrated or arranged rigidly relative to one another, in particular at each of the plurality of actuation units, and respectively one mechanical connection apparatus and one power transmitter are integrated or arranged rigidly relative to one another at the communications unit.

What was explained above for the optional integration or rigid arrangement relative to one another of the connection apparatuses and the signal transmitters or signal receivers applies accordingly.

In the case of a foot actuation system as described herein, the communications unit further comprises, in particular, a power supply apparatus for supplying power to a plurality of actuation units connected to the communications unit.

In the case of a foot actuation system as described herein, the power supply apparatus of the communications unit comprises, in particular, a battery or an accumulator or a capacitor or any other energy storage device.

In this case, there is no need for a further device, for example a medical device controlled by the foot actuation system, to supply power to the communications unit.

Alternatively, the power supply apparatus of the communications unit can merely comprise a power distribution apparatus for converting and distributing electric power, received, for example, from a medical device controlled by means of the foot actuation system, to the actuation units.

In the case of a foot actuation system as described herein, the control signal transmitter of the communications unit comprises, in particular, a transmitter for wireless transmission of the control signal to a medical device controlled by means of the foot actuation system.

By way of example, the wireless transmission of the control signal is implemented in electromagnetic, optical or acoustic fashion. Numerous frequency bands and numerous modulation methods can be considered for an electromagnetic transmission, as are known, for example, from mobile radio or WLAN or WiFi or Bluetooth or RFID systems. By way of example, an optical transmission is possible in the visible or—preferably—in the infrared or in any other wavelength range. An acoustic transmission is possible in the ultrasonic range, in particular.

If the communications unit comprises a battery or an accumulator or a capacitor or any other energy storage device, which provides all the power required by the foot actuation system, and if it comprises a transmitter for wireless transmission of the control signal, there is no need for a cabled connection between the foot actuation system and the medical device or devices to be controlled by the foot actuation system. Therefore, the outlay for installing a cable, its potential for causing accidents as a "trip hazard", the error sources created by the cable and its detachable connections and the requirement of cleaning the cable are dispensed with.

In the case of a foot actuation system as described herein, the control signal transmitter of the communications unit comprises, in particular, a cable interface for transmitting the control signal by a cable to a medical device controlled by means of the foot actuation system.

The cable can be connected directly or indirectly to the controlled medical device. The cable can further be provided and embodied for transmitting power from the medical device controlled by means of the foot actuation system to the foot actuation system. By way of example, the cable can facilitate the electrical or optical transmission of power, and optionally also of the control signal.

In the case of a foot actuation system as described herein, each actuation unit, in particular, comprises at two sides facing away from one another a respective mechanical connection apparatus for mechanical connection to a respective further actuation unit or to the communications unit.

The arrangement of mechanical connection apparatuses at two sides facing away from one another of each actuation unit can facilitate a linear arrangement of the actuation units and of the communications unit in a straight or curved line.

The communications unit can also comprise at two sides facing away from one another a respective mechanical connection unit for mechanical connection to a respective actuation unit. As a result, the communications unit can be arranged not only at one end of a row of actuation units arranged next to one another but also between actuation units.

Further, each actuation unit can comprise at more than two sides a respective mechanical connection apparatus. By way of example, each actuation unit can have a substantially rectangular base shape and can comprise a mechanical connection apparatus at each side. This can facilitate an arrangement of a plurality or multiplicity of actuation units in a rectangular grid. A corresponding statement applies to the communications unit.

A communications unit for controlling one or more medical devices using a foot comprises a mechanical connection apparatus for releasable mechanical connection to a plurality of actuation units comprising a respective user interface for receiving an actuation information item generated by means of a foot, a signal receiver for receiving a signal representing the actuation information item and a control signal transmitter for transmitting a control signal to a medical device.

A communications unit as described herein is embodied, in particular, to form a foot actuation system as described herein.

The communications unit can comprise a single mechanical connection apparatus for direct releasable mechanical connection to a single actuation units and for indirect mechanical connection to further actuation units or a plurality of mechanical actuation apparatuses for a respective direct releasable mechanical connection to an actuation unit.

An actuation unit for controlling one or more medical devices using a foot comprises a user interface for capturing an actuation information item generated by means of a foot, a mechanical connection apparatus for releasable mechanical connection to a communications unit and a signal transmitter for transmitting a signal representing the actuation information item to the communications unit, wherein the actuation unit is embodied to form a foot actuation system comprising a communications unit and a plurality of actuation units as described herein.

BRIEF DESCRIPTION OF THE FIGURES

Embodiments will be explained in more detail below with reference to the attached figures. In the figures:

FIG. 7 shows a schematic illustration of connection apparatuses of a further foot actuation system;

FIGS. 8A and 8B show schematic illustrations of connection apparatuses of a further foot actuation system.

DESCRIPTION OF THE EMBODIMENTS

Figure 1:
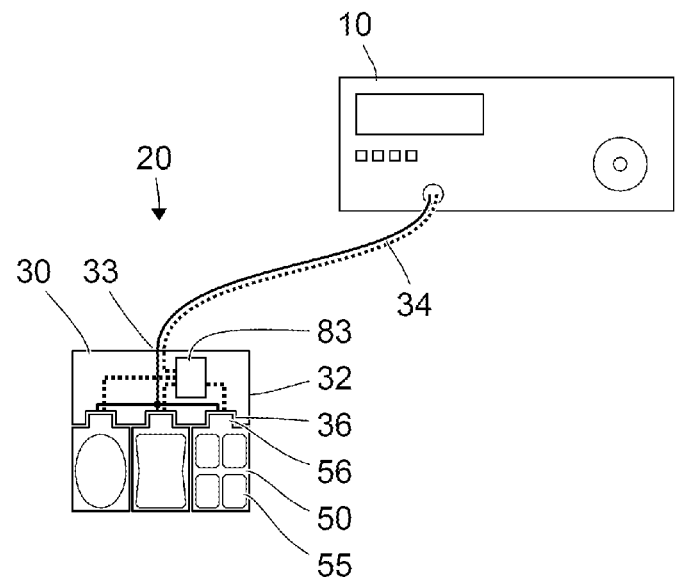
FIG. 1 shows a schematic illustration of a foot actuation system and of a medical device.

FIG. 1 shows a schematic illustration of a medical device 10 and of a foot actuation system 20 for controlling the medical device 10 using a foot. By way of example, the medical device 10 is a light source for an endoscope, an exoscope or a microscope, a camera control unit (CCU), an insufflator or any other pump for supplying or removing a fluid, an electric power source for electrosurgery or any other medical device.

The foot actuation system 20 comprises a communications unit 30 in a housing 32. The communications unit 30 comprises a cable interface 33, which is connected to the medical device 10 by way of a cable 34. Further, the communications unit 30 comprises a plurality of the same mechanical connection apparatuses 36, which are arranged next to one another in a row. Further, the communications unit 30 comprises a circuit 83, which can comprise an integrated circuit, in particular a microprocessor, or which can be embodied as an integrated circuit.

Further, the foot actuation system 20 comprises a plurality of actuation units 50—three in the illustrated example Each actuation unit 50 comprises one or more actuatable surface regions 55 and is embodied to capture a contact with the actuatable surface region or regions 55, an exertion of force or moment on an actuatable surface region 55 and/or a movement of an actuatable surface region 55 as an actuation information item and to generate a signal representing the actuation information item.

In FIG. 1, actuatable surface regions 55 in different forms and number are indicated at the three actuation units 50 in exemplary fashion. The ellipsoid actuatable surface region 55 at the left actuation unit 50 might capture a contact or an exertion of a surface normal force, which exceeds a minimum absolute value, and generate a binary signal representing this actuation information item. Alternatively, the actuation unit 50 illustrated to the left in FIG. 1 might, for example, quantitatively capture the magnitude of the contacted area or the exerted force and generate an analog or digital signal representing this actuation information item, i.e., the magnitude of the contacted area or the exerted force.

In the actuation unit 50 illustrated in the center in FIG. 1, the actuatable surface region 55 might be part of a constituent part of the actuation unit 50 that is pivotable about a horizontal axis. Here, the actuation unit 50 can generate a binary signal which merely distinguishes between two predetermined regions of possible angular positions of the actuatable surface region 55. Alternatively, the actuation unit 50 can distinguish between three or more different regions of possible angular positions of the actuatable surface region 55 and generate a signal representing this actuation information. In particular, the actuation unit 50 illustrated in the center in FIG. 1 can generate an analog signal which is proportional to the angle position of the actuatable surface region 55 or a digital signal representing the actuation information item by virtue of distinguishing between many different possible angular positions or many different small regions of possible angular positions.

Illustrated to the right in FIG. 1 is an actuation unit with a plurality of actuatable surface regions 55—four in the illustrated example. What was explained for the actuation units illustrated to the left and in the center in FIG. 1 applies accordingly to each individual actuatable surface region.

The cable 34 is provided and embodied—as indicated by a solid line—for transmitting electric power from the medical device 10 to the foot actuation system 20. The communications unit 30 transmits power received from the medical device 10 onwards to the actuation units 50. Further, the cable 34 is provided and embodied—as indicated by a dashed line—for transmitting a control signal from the communications unit 30 to the medical device 10.

From the actuation units 50, the communications unit 30 receives signals representing the actuation information items. These signals are processed by the circuit 83 of the communications unit 30. On the basis of the signals received from the actuation units 50, the circuit 83 generates the aforementioned control signal, which is provided at the cable interface 33 and transmitted to the medical device 10 by means of the cable 34. In particular, the control signal contains or represents actuation information items from all actuation units.

The entire foot actuation system 20 is provided for arrangement on the floor of an operating theater, a treatment room in a medical practice or in any other medical establishment.

Figure 2:
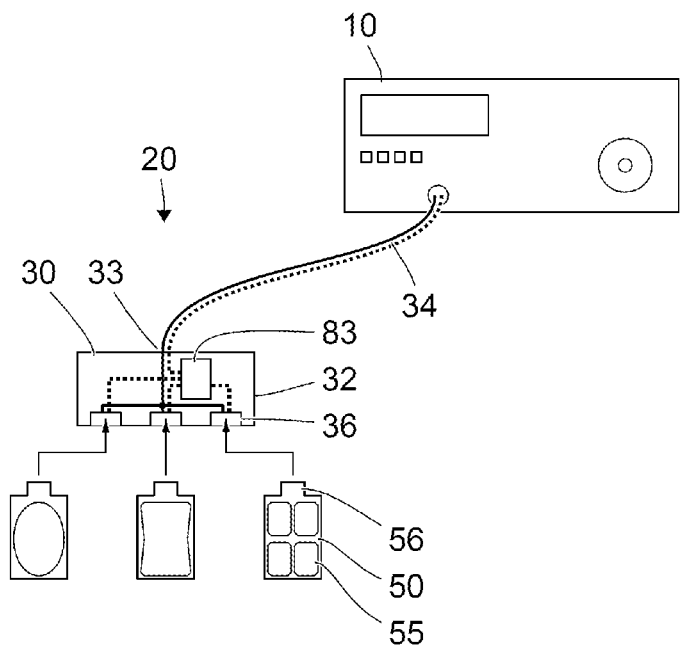
FIG. 2 shows a further schematic illustration of the foot actuation system and of the medical device of FIG. 1.

FIG. 2 shows a further schematic illustration of the medical device 10 and of the foot actuation system 20 of FIG. 1. The illustration in FIG. 2 differs from the illustration in FIG. 1 in that the actuation units 50 are mechanically and spatially separated from the communications unit 30. The mechanical connection apparatuses 36 at the communications unit 30 and mechanical connection apparatuses 56 at the actuation units 50 are embodied for a repeatedly releasable mechanical connection and separation. Each individual actuation unit 50 can be mechanically connected to the communications unit 30 and be nondestructively separated therefrom virtually any number of times. All mechanical connection apparatuses 36 at the communications unit 30 are the same and all mechanical connection apparatuses 56 of the actuation units 50 are the same. This allows each individual actuation unit 50 to be positioned at the communications unit as desired. This, together with a plurality of or many different structures of the actuation units 50, facilitates numerous different configurations of the foot actuation system 20, in which various actuation units are connected in a different number and different arrangements to the communications unit 30.

Deviating from the illustrations in FIGS. 1 and 2, the communications unit 30 might merely have two or four or more mechanical connection apparatuses 36 for releasable mechanical connection to a respective actuation unit 50. Deviating from the illustrations in FIGS. 1 and 2, the mechanical connection apparatuses 36 can be arranged not only in a straight line but also in a curved line or at a plurality of edges of the communications unit 30, in particular in two straight or curved lines at two sides, facing away from one another, of the communications unit 30.

Figure 3:
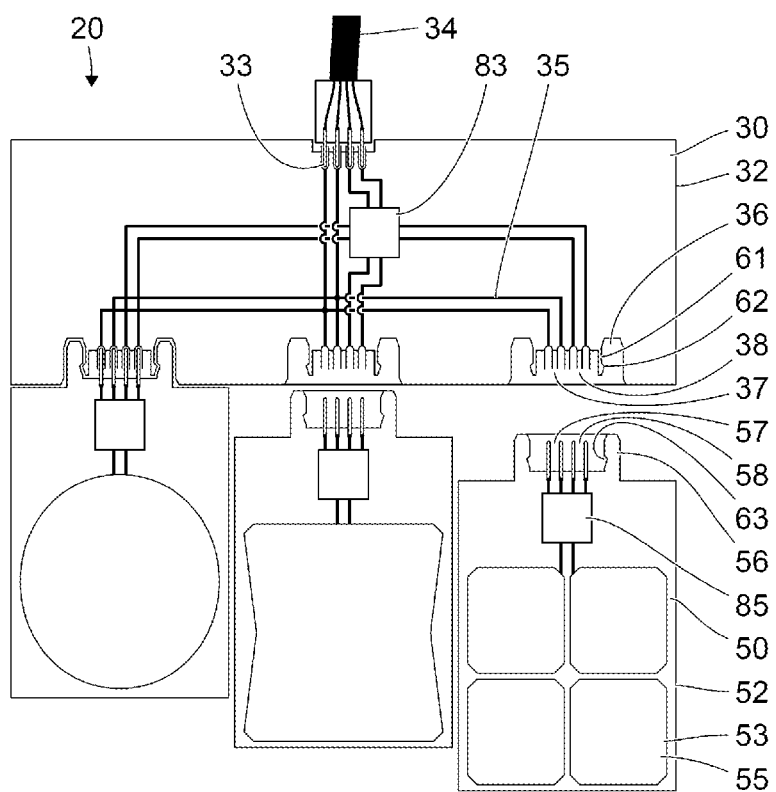
FIG. 3 shows a magnified schematic illustration of the foot actuation system of FIGS. 1 and 2.

FIG. 3 shows a further schematic and magnified illustration of the foot actuation system 20 of FIGS. 1 and 2. The plane of the drawing in FIG. 3 is parallel to a floor, on which the foot actuation system rests in the orientation provided for use.

Deviating from the illustrations in FIGS. 1 and 2, the actuation units 50 are illustrated with different spatial and mechanical relationships with respect to the communications unit 30. The actuation unit 50 illustrated far left in FIG. 3 is mechanically connected to the communications unit 30. The actuation unit 50 illustrated far right in FIG. 3 is mechanically and plainly physically separated from the communications unit 30. The actuation unit 50 illustrated in the center in FIG. 3 is mechanically separated from the communications unit 30 in FIG. 3 but arranged spatially adjacent to the latter.

The contours of the housing 32 of the communications unit 30, the contours of the housings 52 of the actuation units 50 and the contours of the actuatable surface regions 55 of the actuation units 50 are illustrated in FIG. 3 Incidentally, apparatuses of the communications unit 30 and of the actuation units 50 which are not visible from the outside, in particular concealed in the interior of the housings 32, 52, are illustrated in FIG. 3.

In the example shown in FIG. 3, the cable interface 33 is embodied as a plug-in connector with a plurality of plug-in connections, each electrically conductive, for transmitting electric power and a control signal. In the example illustrated in FIG. 3, the cable interface 33 comprises four individual electrical plug-in connections, of which the two left connections are embodied to transmit electric power from the medical device 10 to the communications unit 30 (cf. FIG. 1: the solid line of the cable 34) and the two right connections are embodied to transmit a control signal from the communications unit 30 to the medical device 10 (cf. FIG. 1: the dashed line).

The communications unit 30 comprises a power distribution apparatus 35 for distributing the electric power received by the cable 34 among the actuation units 50.

A power transmitter 37 and a signal receiver 38 are integrated with each mechanical connection apparatus 36 at the communications unit 30. In the illustrated example, the power transmitter 37 and the signal receiver 38 are each formed from a pair of individual electrical plug-in connectors. The left pair of electrical plug-in connectors forms the power transmitters 37 in each case; the right pair of electrical plug-in connectors forms the signal receiver 38 in each case.

The power transmitters 37 at all mechanical connection apparatuses 36 are connected to the cable interface 33 via the power distribution apparatus 35. In the illustrated example, the power distribution apparatus 35 merely forms a parallel circuit of the power transmitters 37 at all mechanical connection apparatuses 36. Deviating from the illustration in FIG. 3, provision can be made of circuits for galvanic isolation, for transforming current and voltage, for stabilization and/or for converting direct current into alternating current, or vice versa.

The signal receivers 38 at all mechanical connection apparatuses 36 are connected to signal inputs of the circuit 83 of the communications unit 30. A signal output of the circuit 83 is connected to the cable interface 33 of the communications unit 30. The circuit 83 of the communications unit 30 can likewise be supplied with power received via the cable 34.

Each actuation unit 50 comprises a power receiver 57 and a signal transmitter 58 at its mechanical connection apparatus 56—integrated with the mechanical connection apparatus 56 in the illustrated example. The power receiver 57 at each actuation unit 50 corresponds to the power transmitter 37 at each mechanical connection apparatus 36 of the communications unit 30, i.e., it is complementary to the latter. The signal transmitter 58 of each actuation unit 50 corresponds to the signal receiver 38 at each mechanical connection apparatus 36 of the communications unit 30, i.e., it is complementary to the latter. In particular, the power transmitter 37 at each mechanical connection apparatus 36 of the communications unit 30 on the one hand and the power receiver 57 of each actuation unit 50 are embodied as corresponding plug-in connectors and the signal receiver 38 at each mechanical connection apparatus 36 of the communications unit 30 on the one hand and the signal transmitter 58 of each actuation unit 50 are embodied as corresponding electrical plug-in connectors.

In the illustrated example, each actuation unit 50 comprises a circuit 85, in particular an integrated circuit, which can be embodied as a microprocessor or can contain a microprocessor. The circuit 85 of each actuation unit 50 is embodied to obtain an actuation information item, specifically to capture whether the actuatable surface region 55 or one of the plurality of actuatable surface regions 55 of the actuation unit is contacted or exposed to a force or a moment and optionally also to capture the size of the contacted area or the magnitude of the exerted force or the exerted moment. The circuit 85 of each actuation unit 50 is embodied to generate a signal representing this actuation information item. This signal is transmitted by the signal transmitter 58 of the actuation unit 50 and the signal receiver device 38 of the communications unit 30 to the circuit 83 of the communications unit 30. The signals received from all actuation units 50 mechanically connected to the communications unit 30 are transmitted by the circuit 83 of the communications unit 30 via the cable interface 33 and the cable 34 to the medical device 10 (cf. FIGS. 1, 2) in unaltered or prepared fashion. Preparation of the signals by the circuit 83 of the communications unit 30 can comprise filtering, digitization, prioritization, conversion into a (different) protocol, etc.

In the example illustrated in FIG. 3, the mechanical connection apparatuses 36 of the communications unit 30 are embodied as cutouts or grooves, in which the power transmitter 37 and the signal receiver 38 are arranged in each case, and the mechanical connection apparatuses 56 of the actuation units 50 are embodied as convex regions, which engage in these grooves or cutouts. The mechanical connection apparatuses 36, the power transmitters 37 and the signal receivers 38 at the communications unit 30 and the mechanical connection apparatuses 56, the power receiver 57 and the signal transmitters 58 at the actuation units 50 are embodied in such a way that, in the case of complete insertion of the mechanical connection apparatus 56 of an actuation unit 50 in a mechanical connection apparatus 36 of the communications unit 30, the power transmitter 37 of the communications unit 30 is coupled to the power receiver 57 of the actuation unit 50 and, at the same time, the signal receiver 38 of the communications unit 30 is coupled to the signal transmitter 58 of the actuation unit 50, in each instance in such a way that a transmission of power and signals is possible.

In the illustrated example, two flexurally elastic tongues 61, each with a latching lug 62, are provided at each mechanical connection apparatus 36 of the communications unit 30 and cutouts 63 are provided at the mechanical connection apparatus 56 of each actuation unit 50. In the provided arrangement of the actuation unit 50 at the communications unit 30, shown in the left actuation unit in FIG. 3, the latching lugs engage in the corresponding cutouts 63. A separation of the actuation unit 50 from the communications unit 30 requires an elastic deformation of the tongues 61. The elastic restoration forces of the flexurally elastic tongues 61 counteract a separation of the actuation unit 50 from the communications unit 30. However, if the elastic restoration forces of the flexurally elastic tongues 61 are overcome, the actuation unit 50 can be separated from the communications unit 30.

Figure 4:
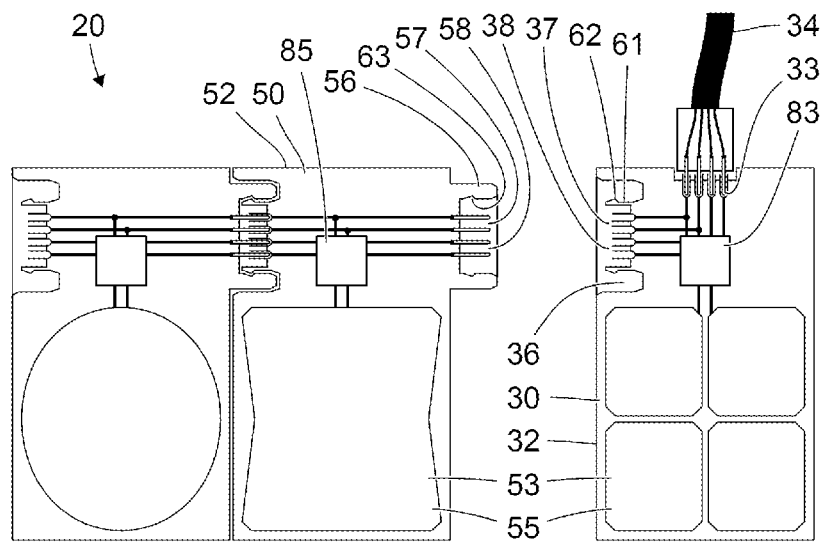
FIG. 4 shows a schematic illustration of a further foot actuation system.

FIG. 4 shows a schematic illustration of a further foot actuation system 20, which is similar to the foot actuation system illustrated on the basis of FIGS. 1 to 3 in terms of a few features, properties and functions. Described below are, in particular, features, properties and functions of the foot actuation system shown in FIG. 4 in which the latter differs from the foot actuation system illustrated on the basis of FIGS. 1 to 3.

The foot actuation system 20 shown in FIG. 4 differs from the foot actuation system illustrated on the basis FIGS. 1 to 3 in that, in particular, each actuation unit comprises a plurality of mechanical connection apparatuses 56. In the illustrated example, each actuation unit 50 has a respective mechanical connection apparatus 56 on two sides facing away from one another, specifically on a side illustrated to the left in FIG. 4 and on a side illustrated to the right in FIG. 4. Integrated in each mechanical connection apparatus 56 of an actuation unit there respectively is a power receiver 57 and a signal transmitter 58 (specifically respectively at the right mechanical connection apparatus in FIG. 4) or a power transmitter and a signal receiver (specifically respectively at the left side of each actuation unit 50 in FIG. 4). In the illustrated example, the mechanical connection apparatus 56 arranged on the right at each actuation unit 50 corresponds to the mechanical connection apparatus of each actuation unit of the foot actuation system illustrated on the basis of FIGS. 1 to 3.

In the foot actuation system 20 shown in FIG. 4, the communications unit 30 only has one mechanical connection apparatus 36. In the illustrated example, this mechanical connection apparatus 36 of the communications unit 30 corresponds to the mechanical connection apparatuses of the communications unit of the foot actuation system illustrated on the basis of FIGS. 1 to 3.

In the illustrated example, the mechanical connection apparatus illustrated to the left at each actuation unit 50 corresponds to the mechanical connection apparatuses of the communications unit of the foot actuation system illustrated on the basis of FIGS. 1 to 3 and to the mechanical connection apparatus 36 of the communications unit 30 shown in FIG. 4. Therefore, the mechanical connection apparatus, respectively illustrated on the left in FIG. 4, of each actuation unit 50 has not been provided with a reference sign.

The mechanical connection apparatuses 56 respectively arranged to the right at the actuation units 50 are complementary to the connection apparatuses respectively arranged to the left at the actuation units 50, and so a plurality of actuation units 50 arranged next to one another in a row can be directly mechanically interconnected, in each case in pairs. To be able to provide reference signs to the features of the mechanical connection apparatuses 36, 56 and of the power transmitters 37, signal receivers 38, power receivers 57 and signal transmitters integrated therein, the communications unit 30 has been shown mechanically separated and spaced apart from the actuation units 50. Proceeding from this configuration shown in FIG. 4, the actuation units 50 can be moved toward the communications unit 30 and can be mechanically connected to the latter and can be coupled therewith in respect of the transmission of power and signals.

Deviating from the illustration in FIG. 4, the communications unit 30 can have one or more further mechanical connection apparatuses for direct and releasable mechanical connection to respectively one actuation unit. By way of example, a mechanical connection apparatus corresponding to the mechanical connection apparatuses provided at the respective right of the actuation units 50 in FIG. 4 can be provided at the side of the communications unit 30 illustrated on the right in FIG. 4. Hence, one or more actuation units could also be arranged at the right-hand side of the communications unit 30 and be mechanically connected directly or indirectly to the communications unit 30.

The communications unit 30 illustrated in FIG. 4 further differs from the communications unit of the foot actuation system illustrated on the basis of FIGS. 1 to 3 in that it has itself a plurality of actuatable surface regions 55 at a plurality of components 53 that are movable relative to the housing 32 of the communications unit 30. Consequently, the communications unit 30 is an actuation unit at the same time.

Deviating from the illustration in FIG. 4, the communications unit 30 can also have more or fewer actuatable surface regions 55, in particular only one or no actuatable surface region 55.

Figure 5:
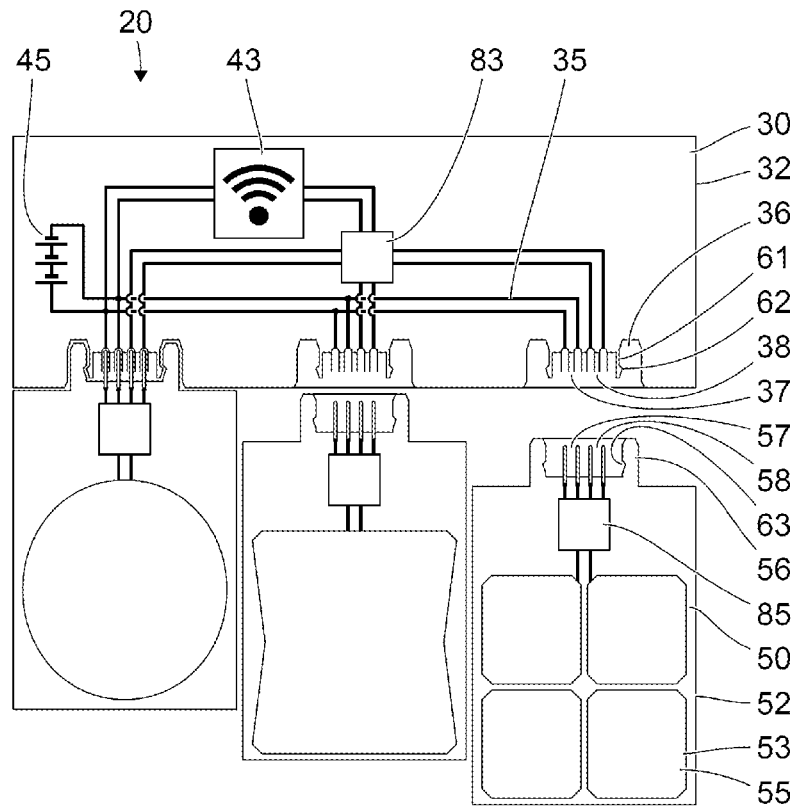
FIG. 5 shows a schematic illustration of a further foot actuation system.

FIG. 5 shows a schematic illustration of a further foot actuation system 20, which is similar to, or the same as, the foot actuation systems illustrated on the basis of FIGS. 1 to 4 in terms of a few features, properties and functions. The type of illustration in FIG. 5 corresponds to that of FIGS. 3 and 4. Described below are, in particular, features, properties and functions of the foot actuation system 20 shown in FIG. 5, by means of which the latter differs from the foot actuation systems illustrated on the basis of FIGS. 1 to 4.

In the foot actuation system shown in FIG. 5, the communications unit 30 comprises a transmitter 43 for wireless transmission of a control signal to the medical device 10 (cf. FIGS. 1, 2) and a dedicated power source 45. The power source 45 comprises one or more battery or accumulator cells, one or more capacitors, fuel cells or any other energy storage devices. The power source 45 supplies electric power to the transmitter 43 of the communications unit 30, the actuation units 50 and, optionally, also the circuit 83 via the power distribution device 35.

The foot actuation system 20 shown in FIG. 5 can be operated with a medical device without a cabled connection. This can simplify the installation in an operating theater or any other medical treatment room and can reduce the risk of damage or the risk of an accident.

Deviating from the illustration in FIG. 5, the actuation units 50 can be provided and embodied for a direct mechanical connection to one another, in a manner similar to the foot actuation system illustrated on the basis of FIG. 4. Here, the communications unit 30 can be embodied for direct mechanical connection to only one actuation unit 50 or to a plurality of actuation units 50 and can itself have one or more actuatable surface regions 55.

In the foot actuation systems illustrated on the basis of FIGS. 1 to 5, latching connections 61, 62, 63 hold the actuation units 50 against the communications unit or against one another (cf. FIG. 4). Alternatively, the mechanical connection apparatuses 36, 56 at the communications unit 30 and at the actuation units 50 can have different features to align the communications unit 30 and the actuation units 50 relative to one another and to releasably interconnect these.

Figure 6:
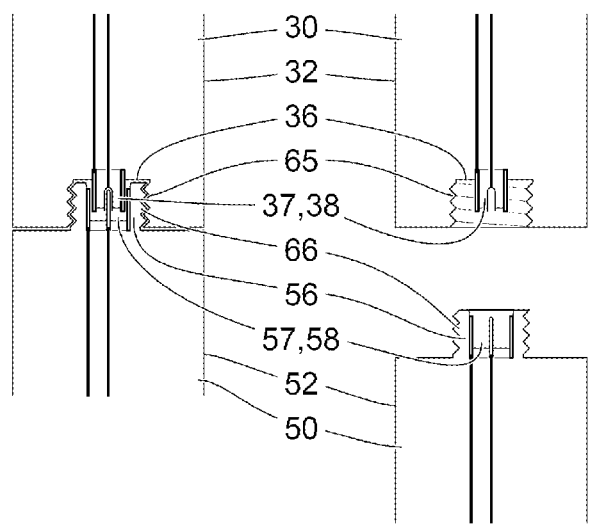
FIG. 6 shows a schematic illustration of connection apparatuses of a further foot actuation system.

FIG. 6 shows two schematic illustrations, each of a communications unit 30 and an actuation unit 50. The type of illustration in FIG. 6 largely corresponds to that of FIGS. 3 to 5. In particular, the plane of the drawing is parallel to a floor on which the foot actuation system 20 rests as intended, and the housings 32, 52 of the communications unit 30 and of the actuation unit 50 are illustrated in transparent fashion, i.e., only indicated by contours. The communications unit 30 and the actuation unit 50 are each shown twice, to be precise in mechanically connected fashion to the left in FIG. 6 and in mechanically separated and spaced apart fashion to the right FIG. 6. Only features in the surroundings of the mechanical connection apparatuses 36, 56 are illustrated in both the communications unit 30 and the actuation unit 50. Further circuits, interfaces, actuatable surface regions, etc. are not shown in FIG. 6.

The mechanical connection apparatus 36 of the communications unit 30 comprises a female thread 65. The mechanical connection apparatus 56 of the actuation unit 50 has a male thread 66 corresponding to the female thread 65 of the mechanical connection apparatus 36 of the communications unit 30.

In the example illustrated in FIG. 6, the power transmitter 37 and the signal receiver 38 of the communications unit 30 are embodied as a coaxial plug, which is arranged coaxially with the female threaded 65 of the communications unit 30, and the power receiver 57 and the signal transmitter 58 of the actuation unit 50 are embodied as a complementary coaxial plug, which is arranged coaxially to the male thread 66 at the actuation unit 50. The actuation unit 50 can be connected to, or separated from, the communications unit 30 by a rotation about an axis, which is parallel to the floor in the case of an intended use of the foot actuation system, by way of a screw-type movement. In so doing, an electrical connection is simultaneously established or separated between, firstly, the power transmitter 37 and the signal receiver 38 of the communications unit and, secondly, the power receiver 57 and the signal transmitter 58 of the actuation unit 50.

In the example illustrated in FIG. 6, the power transmitter 37 and the signal receiver 38 of the communications unit are identical and the power receiver 57 and the signal transmitter 58 of the actuation unit 50 are identical. Both power and a signal representing the actuation information item are transmitted by the same in two cores. By way of example, electric power is transmitted using a direct current component and the signal representing the actuation information item is transmitted using an alternating current component. Alternatively, the communications unit 30 provides, e.g., an electrical DC voltage and captures a current flowing on account of the voltage or a resistance of a switch or of a potentiometer or of any other apparatus in the actuation unit.

FIG. 7 shows a schematic illustration of a further alternative embodiment of a mechanical connection apparatus 36 at a communications unit 30 and of a mechanical connection apparatus 56 at an actuation unit 50, which is similar or corresponds to the examples illustrated on the basis of FIGS. 3 to 6 in terms of some features, properties and functions. The type of illustration in FIG. 7 corresponds to that of FIG. 6. Described below are, in particular, features, properties and functions of the communications unit 30 and actuation unit 50 shown in FIG. 7, by means of which these differ from the examples illustrated above on the basis of FIGS. 3 to 6.

In the communications unit 30 shown in FIG. 7, the mechanical connection apparatus 36 comprises a plurality of concave surface regions 71 at the communications unit 30 and a plurality of magnets 73, and the mechanical connection apparatus 56 and the actuation unit 50 comprises convex surface regions 72 and magnets 75. The concave surface regions 71 of the communications unit 30 and the convex surface regions 72 of the actuation unit 50 are arranged and embodied so as to correspond and be complementary to one another. In the mechanically connected arrangement of the communications unit 30 and of the actuation unit 50, illustrated to the left in FIG. 7, the convex surface regions 72 at the actuation unit 50 engage in the concave surface regions 71 at the communications unit 30 and bring about an interlocking alignment of the actuation unit 50 relative to the communications unit 30.

The magnets 73 in the communications unit 30 and the magnets 75 in the actuation unit 50 are arranged in such a way that they attract each other in the configuration illustrated to the left in FIG. 7 and hold the actuation unit 50 against the communications unit 30.

In the example shown in FIG. 7, too, the power transmitter 37 and the signal receiver 38 of the communications unit 30 are integrated and the power receiver 57 and the signal transmitter 58 of the actuation unit 50 are integrated, similar to the example illustrated in FIG. 6. Like in the example illustrated on the basis of FIG. 6, electric power and a signal representing an actuation information item are transmitted simultaneously by two electric cores.

In the example shown in FIG. 7, the power transmitter 37 and the signal receiver 38 are embodied as a pair of contact areas arranged next to one another. The power receiver 57 and signal transmitter 58 are embodied as a pair of electric contacts arranged next to one another, which are pressed against the contact areas of the power transmitter 37 and signal receiver 38 of the communications unit 30 by way of springs 76.

FIGS. 8A and 8B show schematic illustrations of further examples of a connection between a communications unit 30 and an actuation unit 50, which is similar or corresponds to the examples illustrated on the basis of FIGS. 1 to 7 in terms of some features, properties and functions. The type of illustration in FIGS. 8A and 8B largely correspond to that of FIGS. 3 to 7; however, the plane of the drawing is orthogonal to a floor on which the communications unit 30 and the actuation unit 50 are arranged as intended in FIG. 8A. Described below are, in particular, features, properties and functions of the example shown in FIGS. 8A and 8B, by means of which the latter differs from the examples illustrated on the basis of FIGS. 1 to 7.

The examples shown in FIGS. 8A and 8B differ from the examples illustrated on the basis of FIGS. 3 to 7 in that, in particular, the mechanical connection apparatus 56 of the actuation unit 50 is embodied as a convex surface region 72, specifically as a hook, and the mechanical connection apparatus 36 of the communications unit 30 is embodied as a concave surface region 71 corresponding thereto. In the configuration illustrated in FIG. 8A, the actuation unit 50 and the communications unit 30 are mechanically connected by a form fit of the convex surface region 72 of the actuation unit 50 with the concave surface region 71 of the communications unit 30. Proceeding from the mechanically separated and spaced apart configuration illustrated in FIG. 8B, the actuation unit 50 can initially be inserted into the cutout 71 in the communications unit 30 by way of a movement indicated by an arrow to the right in FIG. 8B and said actuation unit can then be connected in interlocking fashion with the communications unit 30 by lowering the actuation unit 50 (downward in FIG. 8B).

In the examples shown in FIGS. 8A and 8B, the signal transmitter 37 and the signal receiver 38 of the communications unit 30 are integrated and the power receiver 57 and signal transmitter 58 of the actuation unit 50 are integrated, similar to the examples illustrated on the basis of FIGS. 6 and 7. In contrast to the examples illustrated on the basis of FIGS. 3 to 7, the power transmitter 37 and signal receiver 38 of the communications unit 30 are embodied as a coil in the communications unit 30 and the power receiver 57 and signal transmitter 58 of the actuation unit 50 are embodied as a coil in the actuation unit 50 in the example shown in FIGS. 8A and 8B.

In the mechanically connected arrangement present in the case of the intended use of the communications unit 30 and the actuation unit 50, as shown in FIG. 8A, the coil forming the power transmitter 37 and signal receiver 38 of the communications unit 30 and the coil forming the power receiver 57 and signal transmitter 58 of the actuation unit 50 are arranged and oriented relative to one another in such a way that, in inductive fashion, power can be transmitted from the communications unit 30 to the actuation unit 50 and a signal representing an actuation information item can be transmitted from the actuation unit 50 to the communications unit 30.

REFERENCE SIGNS

10 Medical device
20 Foot actuation system for controlling the medical device 10
30 Communications unit of the foot actuation system 20
32 Housing of the communications unit 30
33 Cable interface in the communications unit 30, for receiving power from and for transmitting a control signal by means of a cable 13 to the medical device 10
34 Cable between the communications unit 30 and medical device 10
35 Power distribution apparatus of the communications unit 30
36 Mechanical connection apparatus of the communications unit 30, for releasable mechanical connection to an actuation unit 50
37 Power transmitter of the communications unit 30, for transmitting power to an actuation unit 50
38 Signal receiver of the communications unit 30, for receiving from an actuation unit 50 a signal representing an actuation information item
43 Transmitter of the communications unit 30, for a wireless transmission of a control signal to the medical device 10
45 Power supply apparatus as a power source of the communications unit 30
50 Actuation unit of the foot actuation system 20
52 Housing of the actuation unit 50
53 Component of the actuation unit 50 that is movable relative to the housing 52
55 Actuatable surface region of the actuation unit 50, in particular of the movable component 53
56 Mechanical connection apparatus of the actuation unit 50, for releasable mechanical connection to the power supply and communications unit 30 or to a further actuation unit 50
57 Power receiver of the actuation unit 50, for receiving power from the power supply and communications unit 30 or from a further actuation unit 50
58 Power transmitter of the actuation unit 50, for transmitting a signal representing an actuation information item to the power supply and communications unit 30 or to a further actuation unit 50
61 Flexurally elastic tongue at the communications unit 30
62 Latching lug at the flexurally elastic tongue 61
63 Cutout for receiving the latching lug 62
65 Female thread at the communications unit 30
66 Male thread at the actuation unit 50
71 Concave surface region at the communications unit 30
72 Convex surface region at the actuation unit 50
73 Magnet in the communications unit 30
75 Magnet in the actuation unit 50
76 Spring of the power receiver 57 and signal transmitter 58
83 Circuit in the communications unit 30
85 Circuit in the actuation unit 50

We claim:

1. A foot actuation system for controlling one or more medical devices using a foot, comprising:
a communications unit; and
a plurality of actuation units;
wherein each actuation unit comprises a user interface for capturing an actuation information item generated by means of a foot, an actuation unit mechanical connection apparatus for releasable mechanical connection to the communications unit and a signal transmitter for transmitting a signal representing the actuation information item;
wherein the communications unit comprises a communications unit mechanical connection apparatus for releasable mechanical connection to a plurality of actuation units, a signal receiver for receiving the signals representing the actuation information items, and a control signal transmitter for transmitting a control signal to a medical device; and
wherein the communications unit comprises a power transmitter for transmitting power to the plurality of actuation units and wherein each of the plurality of actuation units comprises a power receiver for receiving power from the communications unit.

2. A foot actuation system according to the preceding claim, wherein the communications unit comprises a plurality of communications unit mechanical connection apparatuses side by side for releasable mechanical connection to a respective actuation unit.

3. A foot actuation system according to claim 1, wherein the actuation unit mechanical connection apparatus and the signal transmitter are integrated or arranged fixedly relative to one another at each of the plurality of actuation units, respectively one actuation unit mechanical connection apparatus and one signal transmitter are integrated or arranged rigidly relative to one another at the communications unit.

4. A foot actuation system according to claim 1, wherein the actuation unit mechanical connection apparatus and the power receiver are integrated or arranged rigidly relative to one another at each of the plurality of actuation units, respectively one actuation unit mechanical connection apparatus and one power transmitter are integrated or arranged fixedly relative to one another at the communications unit.

5. A foot actuation system according to claim 1, wherein the control signal transmitter of the communications unit comprises a transmitter for wireless transmission of the control signal to the medical device that is controlled by means of the foot actuation system.

6. A foot actuation system according to claim 1, wherein each actuation unit comprises at two sides facing away from one another a respective actuation unit mechanical connection apparatus for mechanical connection to a respective further actuation unit or to the communications unit.

7. A foot actuation system according to claim 1, wherein the communications unit further comprises a power supply apparatus for supplying power to a plurality of actuation units connected to the communications unit.

8. A foot actuation system according to the preceding claim, wherein the power supply apparatus of the communications unit comprises a battery or an accumulator or a capacitor.

9. A communications unit for controlling one or more medical devices using a foot, comprising:
- a mechanical connection apparatus for releasable mechanical connection to a plurality of actuation units comprising a respective user interface for receiving an actuation information item generated by means of a foot;
- a signal receiver for receiving a signal representing the actuation information item;
- a control signal transmitter for transmitting a control signal to a medical device; and
- a plurality of power transmitters for transmitting power to the plurality of actuation units.

* * * * *